(12) United States Patent
Kim

(10) Patent No.: US 10,172,658 B2
(45) Date of Patent: Jan. 8, 2019

(54) MEDICAL INSERTION APPARATUS

(71) Applicant: Kyungpook National University Industry-Academic Cooperation Foundation, Daegu (KR)

(72) Inventor: Kyoung Tae Kim, Daegu-si (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 255 days.

(21) Appl. No.: 14/467,861

(22) Filed: Aug. 25, 2014

(65) Prior Publication Data
US 2015/0057564 A1      Feb. 26, 2015

(30) Foreign Application Priority Data

| Aug. 26, 2013 | (KR) | ........................ 10-2013-0101078 |
| Mar. 11, 2014 | (KR) | ........................ 10-2014-0028345 |
| Mar. 12, 2014 | (KR) | ........................ 10-2014-0028921 |
| Mar. 24, 2014 | (KR) | ........................ 10-2014-0034202 |
| Mar. 24, 2014 | (KR) | ........................ 10-2014-0034203 |

(Continued)

(51) Int. Cl.
*A61B 17/86* (2006.01)
*A61N 1/05* (2006.01)
(Continued)

(52) U.S. Cl.
CPC .......... *A61B 17/866* (2013.01); *A61B 5/0492* (2013.01); *A61B 5/4836* (2013.01);
(Continued)

(58) Field of Classification Search
CPC . A61B 5/0492; A61B 5/4893; A61B 17/8625; A61B 17/864; A61B 17/866; A61N 1/0551; A61N 1/0558
See application file for complete search history.

(56) References Cited

U.S. PATENT DOCUMENTS 8,348,983 B2 *   1/2013   Neubardt ........... A61B 17/8625
                                                      600/372
2004/0243207 A1   12/2004   Olson et al.
(Continued)

FOREIGN PATENT DOCUMENTS

| KR | 10 2009 0111340 | 10/2009 |
| KR | 10 2014 0003243 | 1/2014 |
| KR | 10 2014 0007143 | 1/2014 |

*Primary Examiner* — Rene Towa
*Assistant Examiner* — H. Q. Nguyen
(74) *Attorney, Agent, or Firm* — Boyle Fredrickson S.C.

(57) ABSTRACT

Provided are a medical insertion apparatus including a screw body to be inserted into a body, and a conductive portion provided in the screw body and including an externally exposed portion, wherein the conductive portion may extend in a longitudinal direction of the screw body and form a single closed loop, and a medical insertion apparatus including a screw body to be inserted into a body, a driver to engage with the screw body to be used to fasten or loosen the screw body, and a conductive portion provided in the screw body and the driver and including an externally exposed portion on one side of the screw body, wherein a portion of the conductive portion disposed in the screw body and another portion of the conductive portion disposed in the driver may be electrically connected to each other.

6 Claims, 20 Drawing Sheets

(30) Foreign Application Priority Data

Mar. 24, 2014 (KR) .................. 10-2014-0034206
Mar. 24, 2014 (KR) .................. 10-2014-0034210

(51) Int. Cl.
*A61B 5/00* (2006.01)
*A61B 17/70* (2006.01)
*A61B 5/0492* (2006.01)
*A61B 17/00* (2006.01)
*A61C 8/00* (2006.01)
*A61N 1/36* (2006.01)
*A61C 19/04* (2006.01)

(52) U.S. Cl.
CPC ............ *A61B 5/4893* (2013.01); *A61B 17/70* (2013.01); *A61B 17/7032* (2013.01); *A61B 17/864* (2013.01); *A61B 17/8625* (2013.01); *A61C 8/0039* (2013.01); *A61N 1/05* (2013.01); *A61N 1/0551* (2013.01); *A61B 2017/00022* (2013.01); *A61B 2017/0073* (2013.01); *A61C 8/0022* (2013.01); *A61C 8/0089* (2013.01); *A61C 19/04* (2013.01); *A61N 1/0558* (2013.01); *A61N 1/36014* (2013.01)

(56) References Cited

U.S. PATENT DOCUMENTS

| | | | |
|---|---|---|---|
| 2005/0055027 A1* | 3/2005 | Yeung | A61B 17/0401 606/75 |
| 2009/0125072 A1 | 5/2009 | Neubardt | |
| 2011/0264151 A1* | 10/2011 | Davis | A61B 17/7035 606/305 |
| 2012/0185001 A1* | 7/2012 | Nayet | A61B 17/8875 606/301 |

* cited by examiner

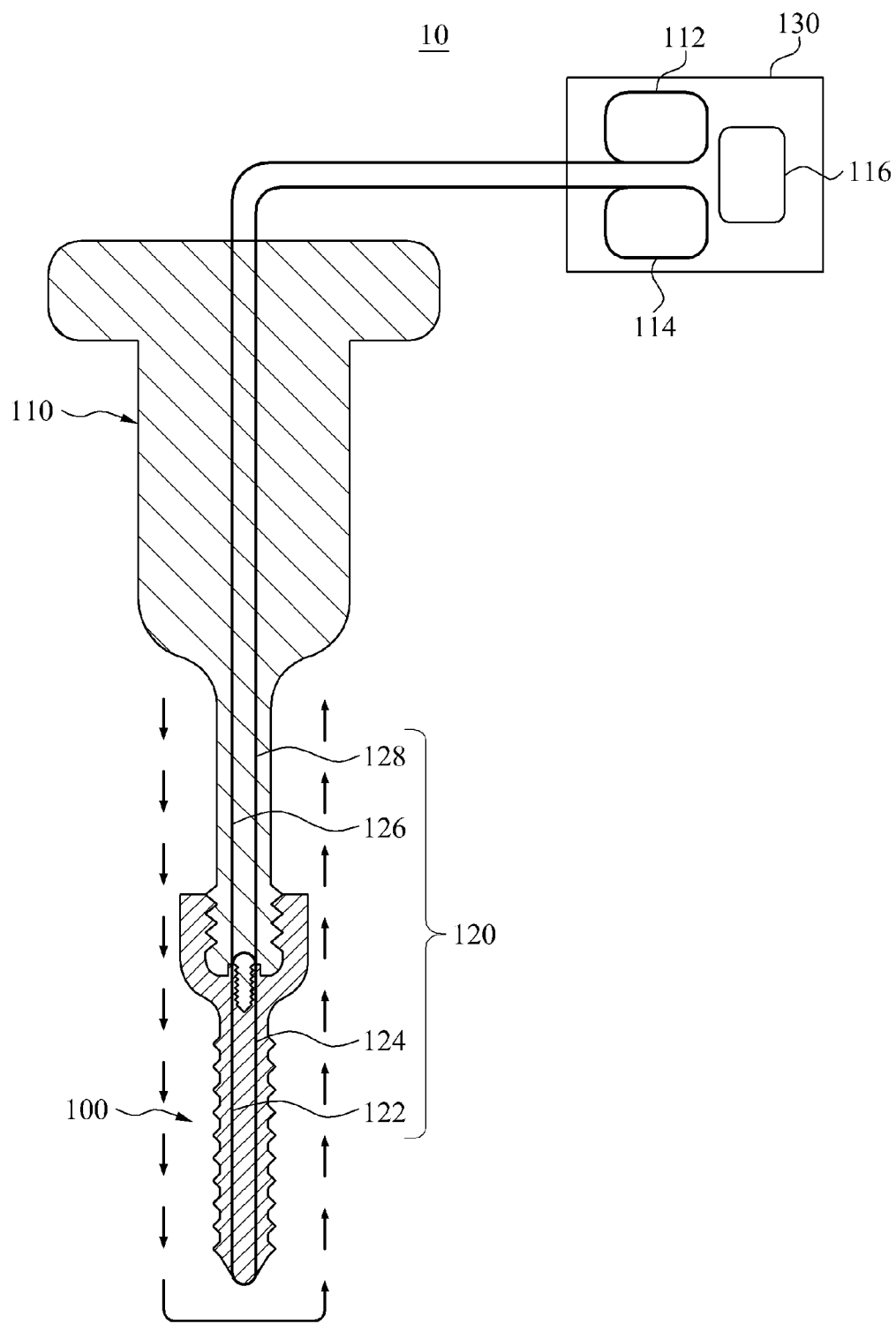

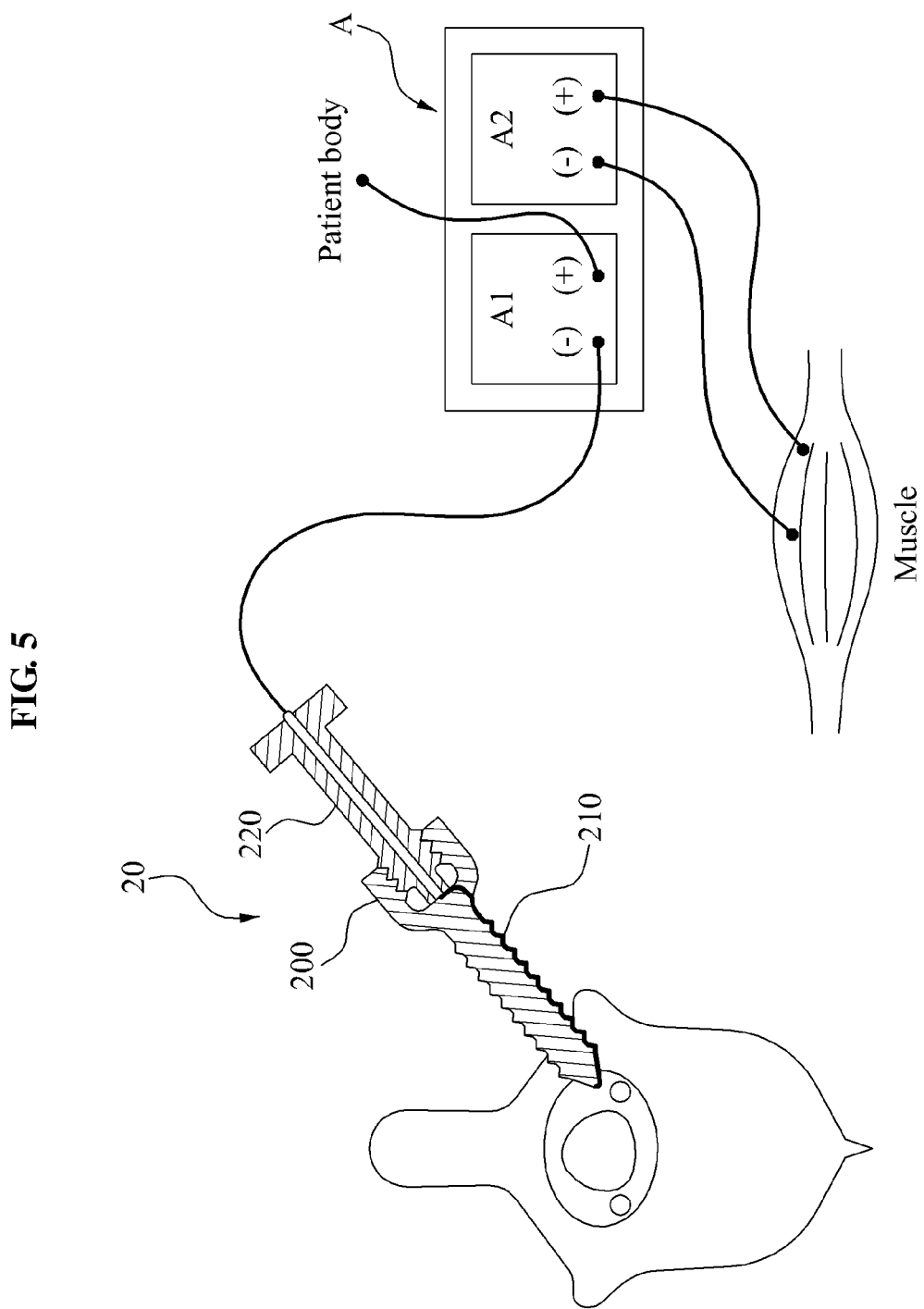

MEDICAL INSERTION APPARATUS

CROSS-REFERENCE TO RELATED APPLICATION

This application claims the benefit of Korean Patent Application Nos. 10-2013-0101078, filed on Aug. 26, 2013, 10-2014-0028345, filed on Mar. 11, 2014, 10-2014-0028921, filed on Mar. 12, 2014, 10-2014-0034206 filed on Mar. 24, 2014, 10-2014-0034210, filed on Mar. 24, 2014, 10-2014-0034202, filed on Mar. 24, 2014, and 10-2014-0034203, filed on Mar. 24, 2014, in the Korean Intellectual Property Office, the disclosures of which are incorporated herein by reference.

BACKGROUND

1. Field of the Invention

Embodiments of the present invention relate to a medical insertion apparatus, and more particularly, to a medical insertion apparatus that may be safely inserted into a body, increase a contact force between a conductor in a screw body and a conductor in a driver, and be efficiently connected to a nerve stimulating and monitoring apparatus.

2. Description of the Related Art

A medical insertion apparatus may be inserted into a body for surgery or treatment.

The medical insertion apparatus may include, for example, a pedicle screw to be inserted into a spine, and an implant to be substituted for a tooth.

A patient with serious spinal stenosis may have surgery to broaden a narrowed spinal canal. By removing an overlying bone or joint and broadening a space, long-pressed nerves may be decompressed, which is referred to as "nerve decompression surgery".

After the decompression surgery, spinal segments may be unstable. When the unstable spinal segments are neglected for a long time, a variety of problems may arise. Thus, the spine may be stabilized by "spinal fusion". The spinal fusion is a process of fixing adjacent vertebrae using pedicle screws and joining the vertebrae into one through bone grafting.

In a case of an implant, additional surgery such as, for example, bone grafting and distraction osteogenesis may be performed on a jawbone from which a tooth is pulled or lost to augment the jawbone to sufficiently surround the implant. A biocompatible implant body may be implanted into the augmented jawbone. Through the foregoing process, a natural tooth function may be recovered.

Recently, spinal or dental treatment or surgery is increasing, and relevant research is being actively conducted.

For example, Korean Patent Application No. 2012-0071311, filed on Jun. 29, 2012, discloses "Dental implant".

SUMMARY

An aspect of the present invention provides a medical insertion apparatus that may detect a contact with a nerve in real time when inserted, thereby preventing neurological damage.

An aspect of the present invention provides a medical insertion apparatus that may detect a contact with a foreign substance including a nerve based on a short circuit principle by forming a single circuit.

An aspect of the present invention provides a medical insertion apparatus that may detect a substance being in contact with a screw body based on a decrement of a current.

An aspect of the present invention provides a medical insertion apparatus that may verify whether a nerve is touched through electromyography (EMG) detection.

An aspect of the present invention provides a medical insertion apparatus that may detect a peripheral nerve when forming a hole to insert a screw body.

An aspect of the present invention provides a medical insertion apparatus that may efficiently detect a nerve and prevent neurological damage by increasing an area of contact with nerves.

An aspect of the present invention provides a medical insertion apparatus that may detect a nerve positioned in a periphery during the entire insertion process.

An aspect of the present invention provides a medical insertion apparatus that may verify a direction in which a nerve is positioned through a conductive portion provided in a predetermined direction.

An aspect of the present invention provides a medical insertion apparatus that may verify a direction of a conductive portion while a screw body is rotating by means of a driver.

An aspect of the present invention provides a medical insertion apparatus that may increase a contact rate of a conductive portion using a tractive force between a screw body and a driver.

An aspect of the present invention provides a medical insertion apparatus that may prevent abrasion of a conductive portion through a surface contact of the conductive portion.

An aspect of the present invention provides a medical insertion apparatus that may include a conductive portion to be manufactured using various metals.

An aspect of the present invention provides a medical insertion apparatus that may increase a surgical stability and reduce a radiation exposure time during surgery.

An aspect of the present invention provides a medical insertion apparatus that may be compatible with an existing nerve stimulating and monitoring apparatus without using separate equipment.

An aspect of the present invention provides a medical insertion apparatus that may wirelessly monitor a nerve using a receiver provided in a driver.

An aspect of the present invention provides a medical insertion apparatus that may reduce an inconvenience that a surgeon may experience due to a wire.

An aspect of the present invention provides a medical insertion apparatus that may include an embedded battery in a driver, the battery to be easily charged by being disposed on a charging stand.

According to an aspect of the present invention, there is provided a medical insertion apparatus including a screw body to be inserted into a body, and a conductive portion provided in the screw body and including an externally exposed portion. The conductive portion may extend in a longitudinal direction of the screw body and forms a single closed loop.

The medical insertion apparatus may further include a driver to engage with the screw body to be used to fasten or loosen the screw body. The conductive portion may be disposed in the driver.

The conductive portion may include a first conductor to extend from one end of the screw body to another end of the screw body, and a second conductor to extend from the other end of the screw body and the one end of the screw body.

The first conductor and the second conductor may be connected to each other, and a portion at which the first conductor and the second conductor are connected to each other may be externally exposed.

The conductive portion may include a third conductor to be connected to the first conductor, and a fourth conductor to be connected to the second conductor. The third conductor and the fourth conductor may be disposed to be spaced apart from each other, and the third conductor and the fourth conductor are disposed in the driver.

The medical insertion apparatus may further include a current generator to apply a current to the third conductor, and a current measurer to measure a current flowing in the fourth conductor. The current generator and the current measurer may be disposed in the driver.

A display with a monitor or a lamp may be provided in the driver to indicate a change in a current flowing in the conductive portion.

The externally exposed portion of the conductive portion may be provided in a ring shape along an outer circumference of the screw body at a position apart from a terminal portion of the screw body.

The screw body may be provided in a form of a tapping screw.

According to an aspect of the present invention, there is provided a medical insertion apparatus including a screw body to be inserted into a body, a driver to engage with the screw body to be used to fasten or loosen the screw body, and a conductive portion provided in the screw body and the driver and including an externally exposed portion on one side of the screw body. A portion of the conductive portion disposed in the screw body and another portion of the conductive portion disposed in the driver may be electrically connected to each other.

The conductive portion may be provided in a form of a wire extending along an outer circumferential surface of the screw body from a top end of the screw body to a central portion of a terminal portion of the screw body.

A display element may be provided in the driver and disposed in a direction identical to a direction of the conductive portion.

The conductive portion may be provided using metal coating on an outer side of the screw body in a longitudinal direction of the screw body.

The conductive portion may include a first conductor provided in the screw body to extend in a longitudinal direction of the screw body, and a second conductor provided in the driver to extend in a longitudinal direction of the driver. The first conductor and the second conductor may be in surface contact with each other.

The first conductor and the second conductor may be externally exposed at a position at which the screw body and the driver are in contact with each other.

A recess into which an end portion of the driver is to be inserted may be provided in the screw body, and the first conductor and the second conductor may be electrically connected to each other in the recess.

The medical insertion apparatus may further include a nerve stimulating and monitoring apparatus to transmit an electrical stimulus to the conductive portion or detect a signal generated by the electrical stimulus.

The conductive portion may include an exposed terminal at one end of the driver, and the nerve stimulating and monitoring apparatus may be connected to the exposed terminal.

A transmitter may be provided in the nerve stimulating and monitoring apparatus, and a receiver may be provided in the driver.

An embedded battery may be provided in the driver, a charging socket may be provided at one end of the driver to charge the embedded battery, and the medical insertion apparatus further include a charging stand on which the charging socket is to be disposed.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which:

FIG. 4 is a view illustrating a medical insertion apparatus connected to an external terminal according to an embodiment of the present invention;

FIG. 5 is a view illustrating a medical insertion apparatus according to an embodiment of the present invention;

DETAILED DESCRIPTION

Figure 1:
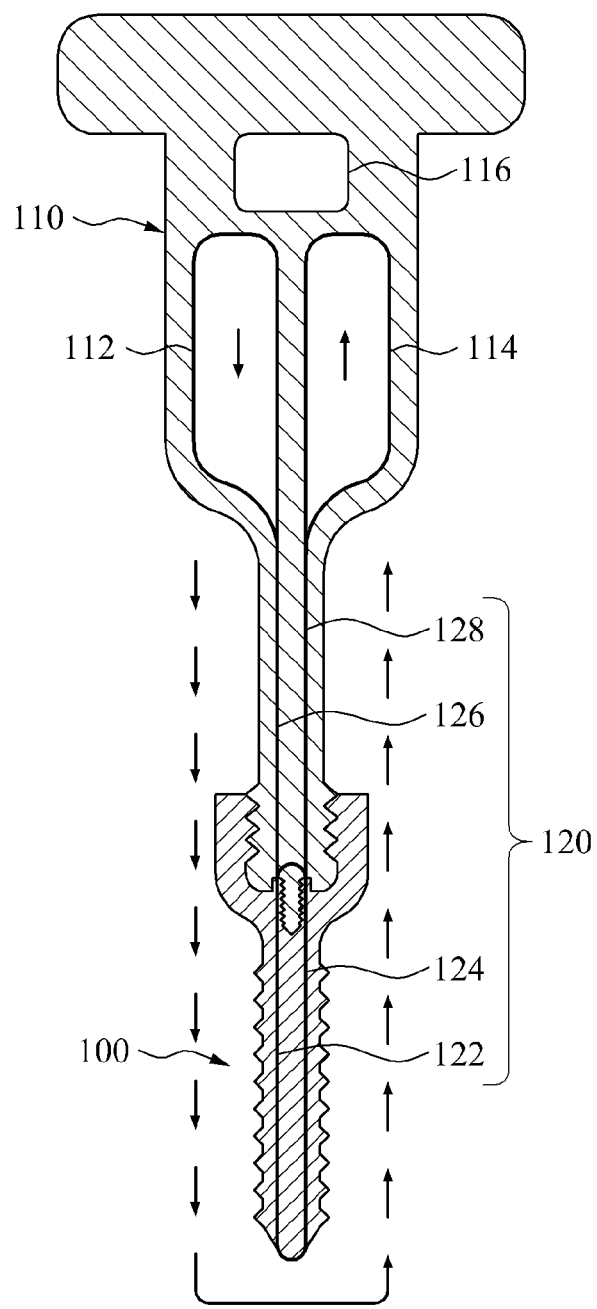
FIG. 1 is a view illustrating a medical insertion apparatus according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

Figure 2:
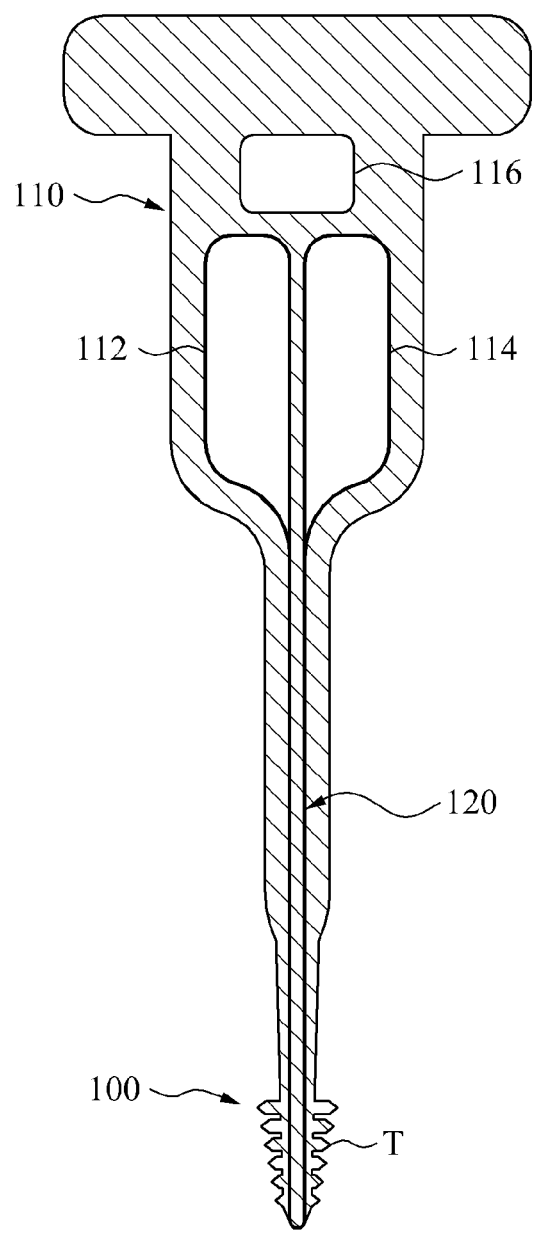
FIG. 2 is a view illustrating a screw body provided in a form of a tapping screw in a medical insertion apparatus according to an embodiment of the present invention.
Figure 3A:
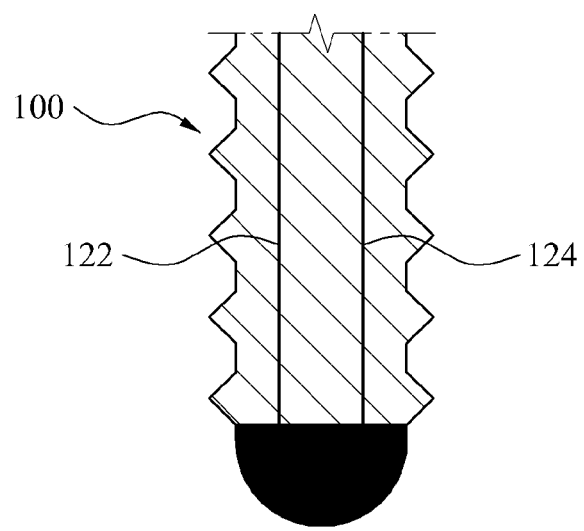
FIGS. 3A and 3B are views illustrating shapes of an externally exposed portion of a screw body in a medical insertion apparatus according to an embodiment of the present invention.
Figure 3B:
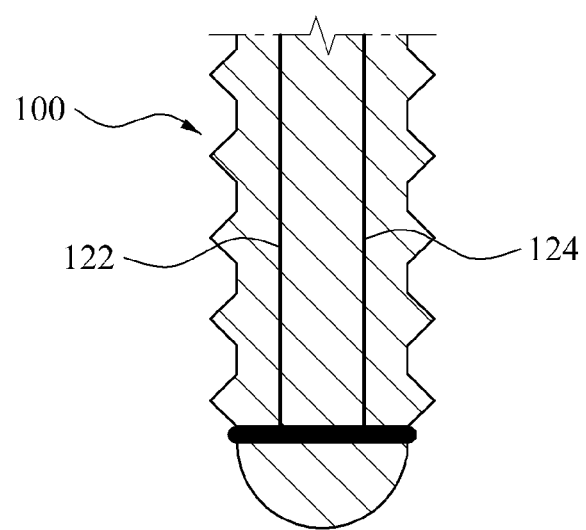

FIG. 1 is a view illustrating a medical insertion apparatus 10 according to an embodiment of the present invention. FIG. 2 is a view illustrating a screw body 100 provided in a form of a tapping screw in the medical insertion apparatus 10 according to an embodiment of the present invention. FIGS. 3A and 3B are views illustrating shapes of an externally exposed portion of the screw body 100 in the medical insertion apparatus 10 according to an embodiment of the present invention. FIG. 4 is a view illustrating the medical insertion apparatus 10 connected to an external terminal 130 according to an embodiment of the present invention.

Referring to FIG. 1, the medical insertion apparatus 10 includes the screw body 100, a driver 110, and a conductive portion 120.

The screw body 100 may be inserted into a body. A thread is provided on an outer side of the screw body 100.

The screw body 100 may be inserted into a spine, a tooth, or a muscle. For example, the screw body 100 may be configured in a synostosis screw to be inserted into an osseous tissue adjacent to a nerve, in particular, a pedicle screw to be inserted into a spine.

Thus, the screw body 100 may be manufactured using titanium. Titanium is excellent in terms of biocompatibility and strength, and thus used as a material for a variety of implants.

To insert the screw body 100 into the body or remove the screw body 100 from the body, the driver 110 is provided to engage with an upper portion of the screw body 100.

The driver 110 engages with the screw body 100 to be used to fasten or loosen the screw body 100.

The driver 110 is connected to a top end of the screw body 100 through screw fastening.

A threaded recess is provided in the upper portion of the screw body 100, and a threaded protrusion having a shape corresponding to a shape of the threaded recess is provided in a lower portion of the driver 110. A threaded protrusion may also be provided in the upper portion of the screw body 100, and a threaded recess having a shape corresponding to a shape of the threaded protrusion may also be provided in the lower portion of the driver 110.

When the screw body 100 and the driver 110 rotate while engaging with each other as described above, the screw body 100 may be inserted into a body to be fixed, or separated from the body.

Referring to FIG. 2, the screw body 100 is provided in a form of a tapping screw T. In this example, the screw body 100 and the driver 110 are integrally provided.

The tapping screw T may be used to perform boring before the screw body 100 is inserted into a body.

The screw body 100 may be inserted into a body more safely through a hole provided by the tapping screw T.

When the screw body 100 and the driver 110 are integrally provided, a battery may be embedded in the medical insertion apparatus 10. Thus, the medical insertion apparatus 10 may be charged for use.

Referring to FIG. 1 again, the conductive portion 120 is disposed in the screw body 100 and the driver 110.

The conductive portion 120 extends in a longitudinal direction of the screw body 100, and forms a single closed loop.

In this example, the conductive portion 120 may include platinum, gold, silver, tungsten, and any material verified to be biocompatible, excellent in electric conductivity, and suitable for detecting a minute electromyography (EMG) signal.

The conductive portion 120 includes a first conductor 122, a second conductor 124, a third conductor 126, and a fourth conductor 128.

The first conductor 122 extends from a top end of the screw body 100 toward a bottom end of the screw body 100. The second conductor 124 extends from the bottom end of the screw body 100 toward the top end of the screw body 100.

The first conductor 122 and the second conductor 124 are connected to each other to form a closed loop.

The first conductor 122 and the second conductor 124 include a portion externally exposed at a terminal portion of the screw body 100.

The portion of the first conductor 122 and the second conductor 124 externally exposed at the terminal portion of the screw body 100 may detect a nerve in a periphery of the screw body 100.

Referring to FIGS. 3A and 3B, the closed loop of the first conductor 122 and the second conductor 124 are externally exposed at the terminal portion of the screw body 100 as follows.

Referring to FIG. 3A, the externally exposed portion of the conductive portion 120 is provided along an outer circumference of the screw body 100.

In detail, an additional member may be provided to completely cover the terminal portion of the screw body 100, or a portion of the closed loop of the first conductor 122 and the second conductor 124 may be provided to completely cover the terminal portion of the screw body 100.

Thus, an area of contact between the conductive portion 120 and nerves at the terminal portion of the screw body 100 may increase, whereby a nerve may be more easily detected.

Referring to FIG. 3B, the externally exposed portion of the conductive portion 120 is provided in a form of a ring shape.

An additional member provided in a form of a ring shape may be disposed to be spaced apart from the terminal portion of the screw body 100. The additional member may be electrically connected to the closed loop of the first conductor 122 and the second conductor 124.

Although FIG. 3B illustrates a single ring shape being disposed in the screw body 100, it is obvious that a plurality of ring shapes may be provided on the screw body 100 to be spaced apart from each other.

As described above, the conductive portion 120 is exposed in a form of a ring shape on a side surface of the screw body 100. Thus, a nerve positioned on the side surface of the screw body 100 may be detected while the screw body 100 is being inserted into a body.

In addition, when combining the configuration of FIG. 3A with the configuration of FIG. 3B, the conductive portion 120 may be configured to detect nerves both at the terminal portion of the screw body 100 and on the side surface of the screw body 100.

The aforementioned closed loop of the first conductor 122 and the second conductor 124 may include an externally exposed portion at the upper portion of the screw body 100.

The portion of the first conductor 122 and the second conductor 124 externally exposed at the upper portion of the screw body 100 may be electrically connected to the conductive portion 120 disposed in the driver 110.

However, it is obvious that the closed loop formed by the first conductor 122 and the second conductor 124 may also be disposed in the screw body 100.

In this example, to electrically connect the closed loop of the first conductor 122 and the second conductor 124 to a portion of the conductive portion 120 disposed in the driver 110, a path for the conductive portion 120 may be provided in the screw body 100.

The third conductor 126 extends from a top end of the driver 110 toward a bottom end of the driver 110, and the fourth conductor 128 extends from the bottom end of the driver 110 toward the top end of the driver 110.

The third conductor 126 is connected to the first conductor 122, and the fourth conductor 128 is connected to the second conductor 124. Also, the third conductor 126 may be connected to the second conductor 124, and the fourth conductor 128 may be connected to the first conductor 122.

Thus, the third conductor 126 and the fourth conductor 128 are disposed to be spaced apart from each other in the driver 110.

As described above, the third conductor 126 and the fourth conductor 128 may respectively be connected to a portion of the closed loop of the first conductor 122 and the second conductor 124.

A current generator 112 and a current measurer 114 are connected to the third conductor 126 and the fourth conductor 128.

The current generator 112 refers to an apparatus that applies a current to the third conductor 126. The current generator 112 may transmit a predetermined amount of current to the third conductor 126.

The current measurer 114 may measure a current flowing in the fourth conductor 128.

Similar to the third conductor 126 and the fourth conductor 128, the current generator 112 and the current measurer 114 are disposed in the driver 110.

However, as shown in FIG. 4, the current generator 112 and the current measurer 114 may be disposed in an external terminal 130. The third conductor 126 and the fourth conductor 128 may be externally exposed through the top end of the driver 110, and connected to the current generator 112 and the current measurer 114 provided in the external terminal 130, respectively.

In this example, the current generator 112 and the current measurer 114 may be relatively easily maintained although defects occur in the current generator 112 and the current measurer 114.

As described above, the conductive portion 120, the current generator 112, and the current measurer 114 may form a single circuit.

When a current is applied from the current generator 112 to the third conductor 126 in a direction of arrows as depicted in FIG. 1, the current may be transmitted from the third conductor 126 to the closed loop of the first conductor 122 and the second conductor 124.

The current may flow toward the terminal portion of the screw body 100 in the longitudinal direction of the screw body 100, change direction at the terminal portion of the screw body 100, and flow toward the upper portion of the screw body 100.

In this example, the fourth conductor 128 may be connected to the second conductor 124, and the current measurer 114 may be connected to the fourth conductor 128. Thus, the current flowing in the second conductor 124 may be measured.

When a current of 5 amperes (A) is measured by the current measurer 114 although a current of 10 A has been applied from the current generator 112 to the closed loop of the first conductor 122 and the second conductor 124, leakage of a current in the closed loop may be verified.

The closed loop of the first conductor 122 and the second conductor 124 includes a portion externally exposed at the terminal portion of the screw body 100. When the externally exposed portion is in contact with, for example, a nerve, a current may leak through the nerve, similar to a short circuit principle.

According to such a principle, when the screw body 100 is inserted into a body and in contact with a foreign substance including a nerve, a contact between the screw body 100 and the nerve may be detected based on a decrement of a current.

When the screw body 100 is in contact with a nerve present in a periphery of a fractured bone, a contact between the screw body 100 and the nerve may be detected. Thus, the fractured bone may be fixed by inserting the screw body 100 to avoid the nerve.

A decrement of a current when the screw body 100 is in contact with a nerve may differ from a decrement of a current when the screw body 100 is in contact with a muscle. Thus, a substance being in contact with the screw body 100 may be detected based on a decrement of a current.

Although not shown in the drawings, a current having leaked through a nerve may generate an EMG signal in a muscle. When the generated EMG signal is detected using a muscle stimulation detector (not shown), the screw body 100 being in contact with a nerve may be verified.

A decrement of a current flowing in the conductive portion 120 forming the closed loop may be verified through the current measurer 114 or the muscle stimulation detector.

The driver 110 further includes a display 116 with a monitor or a lamp.

A decrement of a current may be visually verified through the display 116.

When a current applied from the current generator 112 to the conductive portion 120 and a current measured by the current measurer 114 are displayed on the display 116 using numbers, whether a current is reduced may be easily verified.

When the current measured by the current measurer 114 is lower than the current applied from the current generator 112 to the conductive portion 120, the lamp may be turned on. Thus, whether the current is reduced may be easily verified.

When the current measured by the current measurer 114 is lower than the current applied from the current generator 112 to the conductive portion 120, an alarm may be rung. Thus, whether the current is reduced may be easily verified visually and aurally.

The configuration described above may be applicable to a case in which the screw body 100 is provided in a form of a tapping screw as shown in FIG. 2. The configuration may detect a nerve when forming a hole to insert the screw body 100, thereby preventing neurological damage.

Accordingly, nerves may be doubly detected during the boring process of the screw body 100 and the process of inserting the screw body 100.

As described above, the medical insertion apparatus 10 may detect a contact with nerves when inserted into a body, prevent neurological damage, detect a contact with a foreign substance including a nerve based on a short circuit principle by forming a single circuit, and detect a substance being in contact with a screw body based on a decrement of a current. In addition, the medical insertion apparatus 10 may verify whether a nerve is touched through EMG detection using a current transmitted to the nerve.

Figure 6:
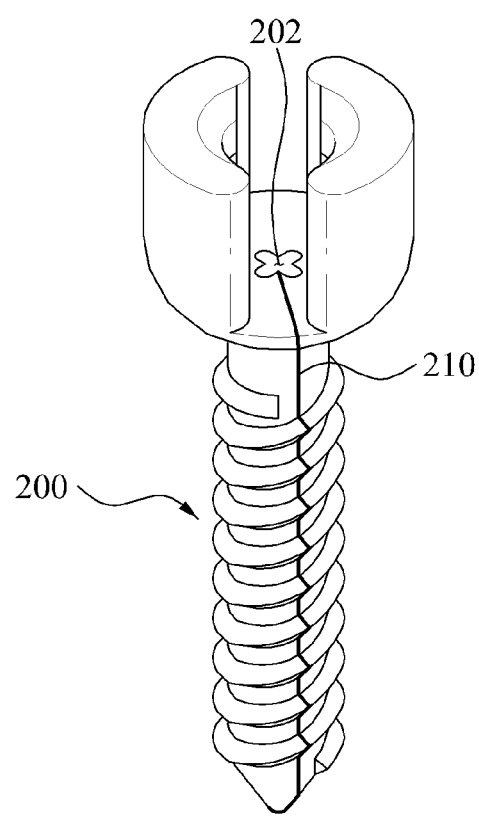
FIG. 6 is a view illustrating a conductive portion disposed in a screw body in a medical insertion apparatus according to an embodiment of the present invention.
Figure 7:
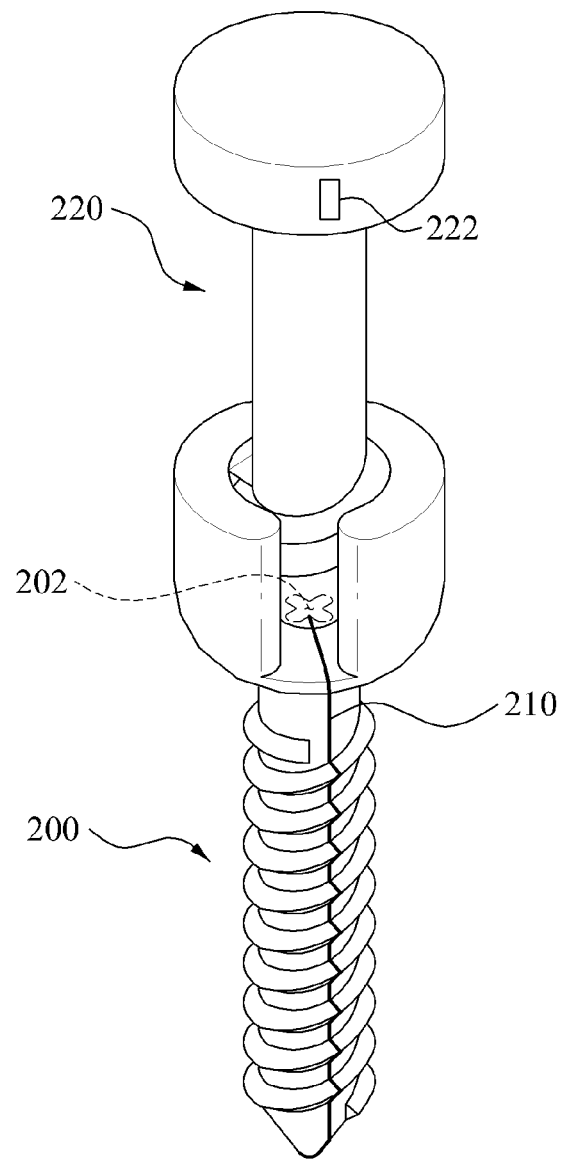
FIG. 7 is a view illustrating a display element disposed in a driver in a medical insertion apparatus according to an embodiment of the present invention.
Figure 8:
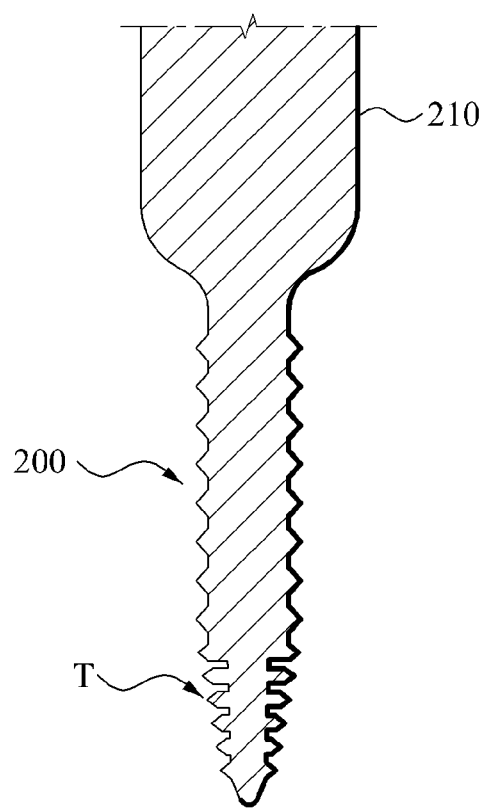
FIG. 8 is a view illustrating a screw body provided in a form of a tapping screw in a medical insertion apparatus according to an embodiment of the present invention.
Figure 9A:
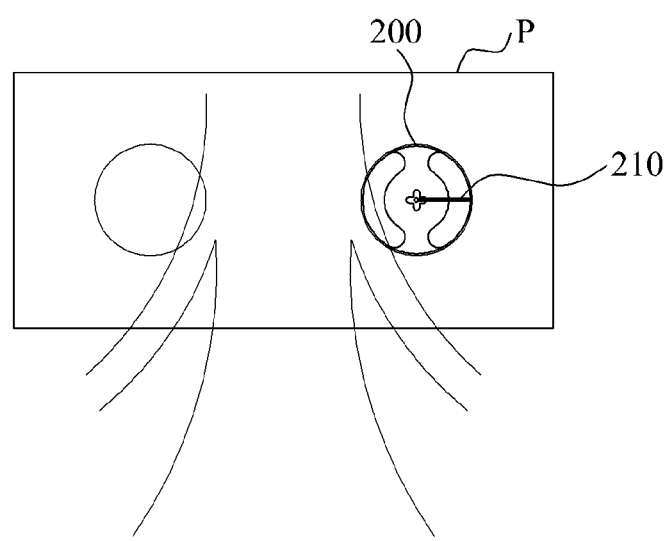
FIGS. 9A and 9B are views illustrating a medical insertion apparatus inserted in a body according to an embodiment of the present invention.
Figure 9B:
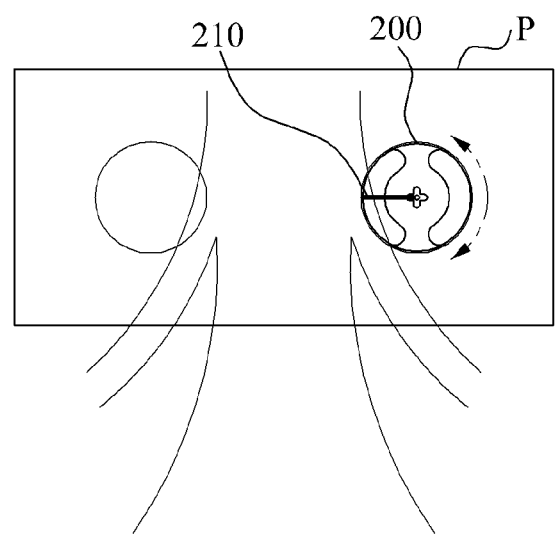

FIG. 5 is a view illustrating a medical insertion apparatus 20 according to an embodiment of the present invention. FIG. 6 is a view illustrating a conductive portion 210 disposed on a screw body 200 in the medical insertion apparatus 20 according to an embodiment of the present invention. FIG. 7 is a view illustrating a display element 222 disposed in a driver 220 in the medical insertion apparatus 20 according to an embodiment of the present invention. FIG. 8 is a view illustrating the screw body 200 provided in a form of a tapping screw in the medical insertion apparatus 20 according to an embodiment of the present invention. FIGS. 9A and 9B are views illustrating the medical insertion apparatus 20 inserted in a body according to an embodiment of the present invention.

Referring to FIG. 5, the medical insertion apparatus 20 includes the screw body 200, the conductive portion 210, and the driver 220.

The medical insertion apparatus 20 may be connected for use to a nerve stimulating and monitoring apparatus A.

The nerve stimulating and monitoring apparatus A may include an apparatus for EMG, an evoked potential (EP) test, a motor evoked potential (MEP) test, and a somatosensory evoked potential (SSEP) test.

However, the nerve stimulating and monitoring apparatus A is not limited thereto. The nerve stimulating and monitoring apparatus A may include any apparatus configured to provide an electrical stimulus to a muscle or nerve, and receive or detect a signal generated in the muscle or nerve in response to the electrical stimulus.

The nerve stimulating and monitoring apparatus A includes a nerve stimulator A1 and a stimulus receptor A2.

The nerve stimulator A1 is a component that applies a minute current directly to a nerve, and the stimulus receptor A2 is a component that detects a signal generated by a current in a nerve or muscle.

The conductive portion 210 provided in the medical insertion apparatus 20 may be connected directly to the nerve stimulator A1, thereby configuring a single electrode to apply a minute current directly to a nerve.

Accordingly, when the conductive portion 210 of the medical insertion apparatus 20 is inserted and in contact with a nerve during surgery or treatment, a current may be applied to the nerve and a signal may be generated in the nerve or muscle. When the generated signal is detected by the stimulus receptor A2, it may be verified that the medical insertion apparatus 20 is in contact with a nerve.

A configuration of the medical inserting apparatus 20 will be described in detail hereinafter.

The screw body 200 may be inserted into a body. A thread is provided on an outer circumferential surface of the screw body 200.

The screw body 200 may be inserted into a spine, a tooth, or a muscle. Thus, the screw body 200 may be manufactured using titanium. Titanium is excellent in terms of biocompatibility and strength, and thus may be used as a material for a variety of implants.

The conductive portion 210 is exposed on an outer side of the screw body 200.

The conductive portion 210 may be provided using a material which is biocompatible and excellent in electric conductivity, for example, platinum, gold, silver, and tungsten.

For example, the conductive portion 210 may be configured by attaching platinum to be exposed on the outer side of the screw body 200. The conductive portion 210 may also be provided by plating the outer side of the screw body 200 with a conductive material.

Using a relatively simple method as described above, the conductive portion 210 may be provided on the screw body 200. Thus, the conductive portion 210 may be easily applicable to an existing screw body.

In addition, the conductive portion 210 may not need to be provided in the screw body 200. Thus, a time and a cost to be used to manufacture the screw body 200 may be reduced.

In detail, referring to FIG. 6, the conductive portion 210 extends in a longitudinal direction of the screw body 200 from a top end of the screw body 200 to a terminal portion of the screw body 200, and extends straightly in the longitudinal direction of the screw body 200 on the outer circumferential surface of the screw body 200.

The conductive portion 210 is provided in a form of a strand of wire. The conductive portion 210 extends along the outer circumferential surface of the screw body 200 from the top end of the screw body 200 to a central portion of the terminal portion of the screw body 200.

As described above, the conductive portion 210 extends in a predetermined direction on the outer circumferential surface of the screw body 200 and is externally exposed in the longitudinal direction of the screw body 200. Thus, the conductive portion 210 may detect a contact with nerves at all positions in the longitudinal direction of the screw body 200.

Accordingly, the medical insertion apparatus 20 may detect a contact between the screw body 200 and a nerve during the whole process, starting from when the insertion of the medical insertion apparatus 20 is initiated until the insertion of the medical insertion apparatus 20 is completed.

When the terminal portion of the screw body 200 is in contact with a nerve, the screw body 200 may slidingly move aside. Since a nerve root may be damaged when the screw body 200 is moved forward by force, an increase in an area of contact between the conductive portion 210 and nerves may be necessary to prevent neurological damage. In such an aspect, the conductive portion 210 may be exposed in the longitudinal direction of the screw body 200 on the outer side of the screw body 200.

The conductive portion 210 is provided in a form of a strand of wire. However, since the screw body 200 rotates to be inserted into a body, the conductive portion 210 may also rotate. Thus, the conductive portion 210 may detect nerves positioned in all directions.

However, a number of conductive portions 210 is not limited thereto. It is obvious that a plurality of conductive portions 210 may be provided on the outer circumferential surface of the screw body 200 and a current may be allowed to flow in each conductive portion 210.

The conductive portion 210 configured as described above is connected directly to the nerve stimulator A1. However, to reduce a unit cost of production of the screw body 200 and facilitate a process of processing a wire connected to the nerve stimulator A1 after the screw body 200 is inserted into a body, the conductive portion 210 may be configured to be connected to the nerve stimulator A1 through a medium of the driver 220.

To achieve the foregoing, the driver 220 is provided to engage with an upper portion of the screw body 200.

The driver 220 may be used to insert the screw body 200 into a body or remove the screw body 200 from a body. The driver 220 may be used to fasten or loosen the screw body 200.

For example, two long extensions may be provided at the top end of the screw body 200, and the driver 220 may be fit between the extensions to fasten or loosen the screw body 200.

A recess may be provided in the upper portion of the screw body 200, and a protrusion having a shape corresponding to a shape of the recess may be provided in a lower portion of the driver 220. A protrusion may also be provided in the upper portion of the screw body 200, and a recess having a shape corresponding to a shape of the protrusion may also be provided in the lower portion of the driver 220.

When the screw body 200 and the driver 220 rotate while engage with each other as described above, the screw body 200 may be inserted into a body to be fixed, or separated from the body.

In this example, the driver 220 may be electrically connected to the conductive portion 210 provided on the screw body 200.

To ensure an electrical connection between the driver 220 and the conductive portion 210, an end portion of the driver 220 may be inserted into the screw body 200.

In detail, the conductive portion 210 is connected to one side of a recess 202 at the top end of the screw body 200. Thus, when the driver 220 is fastened to the recess 202, the conductive portion 210 and the driver 220 may be electrically connected to each other.

The driver 220 includes a display element 222.

The display element 222 may be provided in any form if a direction of the conductive portion 210 is visually verifiable.

Referring to FIG. 7, the display element 222 is disposed in a direction identical to the direction of the conductive portion 210 when the driver 220 is initially fastened to the recess 202 of the screw body 200.

Thus, when the driver 220 rotates while being fastened to the screw body 200, the display element 222 provided in the driver 220 and the conductive portion 210 may face an identical direction.

Accordingly, by verifying a direction of the display element 222, the direction of the conductive portion 210 when the screw body 200 is inserted into a body may be verified.

In addition, the direction of the conductive portion 210 when the conductive portion 210 is in contact with a nerve may be verified. Thus, a direction in which the nerve is positioned may also be verified. Thus, neurological damage may be minimized when the screw body 200 is inserted into a body.

The medical insertion apparatus 20 configured as described above may be used as a device to perform boring before the screw body 200 is inserted into a body.

Referring to FIG. 8, the screw body 200 is provided in a form of a tapping screw T.

The screw body 200 may be inserted into a body more safely through a hole provided by the tapping screw T.

As described above, when the conductive portion 210 is disposed on the outer circumferential surface of the screw body 200 provided in the form of the tapping screw T, neurological damage occurring during a boring process may be prevented.

The medical insertion apparatus 20 may be inserted into a body and detect a nerve as follows.

The driver 220 may be fastened to the recess 202 at the top end of the screw body 200. The driver 220 and the conductive portion 210 connected to the recess 202 may be electrically connected to each other.

By rotating the driver 220, the screw body 200 may initiate insertion into a body.

As shown in FIGS. 9A and 9B, the conductive portion 210 provided on one side of the outer circumferential surface of the screw body 200 may or may not be in contact with a nerve.

FIGS. 9A and 9B will be described based on a case in which the medical insertion apparatus 20 is inserted into a body through a hole provided on a spine fixation plate P.

The conductive portion 210 is provided on the outer side of the screw body 200 with a predetermined directivity. Thus, when the conductive portion 210 faces a direction differing from a direction in which a nerve is positioned as shown in FIG. 9A, the conductive portion 210 may not be in contact with the nerve.

Conversely, when the conductive portion 210 faces a direction identical to the direction in which the nerve is positioned as shown in FIG. 9B, the conductive portion 210 may be in contact with the nerve.

When the conductive portion 210 is in contact with a nerve in a predetermined direction, the direction in which the nerve is positioned may be verified. Thus, the screw body 200 may be inserted at a position relatively far apart from the direction.

When the conductive portion 210 is in contact with a nerve, a current from the nerve stimulator A1 may be transmitted to the nerve. The current applied to the nerve may generate a signal in a muscle or the nerve, and the generated signal such as, for example, an EMG signal may be detected in the muscle or the nerve by the stimulus receptor A2.

Thus, when the screw body 200 is in contact with a nerve, a current may be applied and a signal may be generated in a muscle. By detecting the generated signal using the stimulus receptor A2, the contact between the screw body 200 and the nerve may be verified in real time.

As described above, the medical insertion apparatus 20 may efficiently detect a nerve by increasing an area of contact with nerves, prevent neurological damage, detect nerves positioned in a periphery during the whole insertion process, verify a direction in which a nerve is positioned through a conductive portion provided in a predetermined direction, and verify a direction of the conductive portion while a screw body is rotating by means of a driver.

Figure 10:
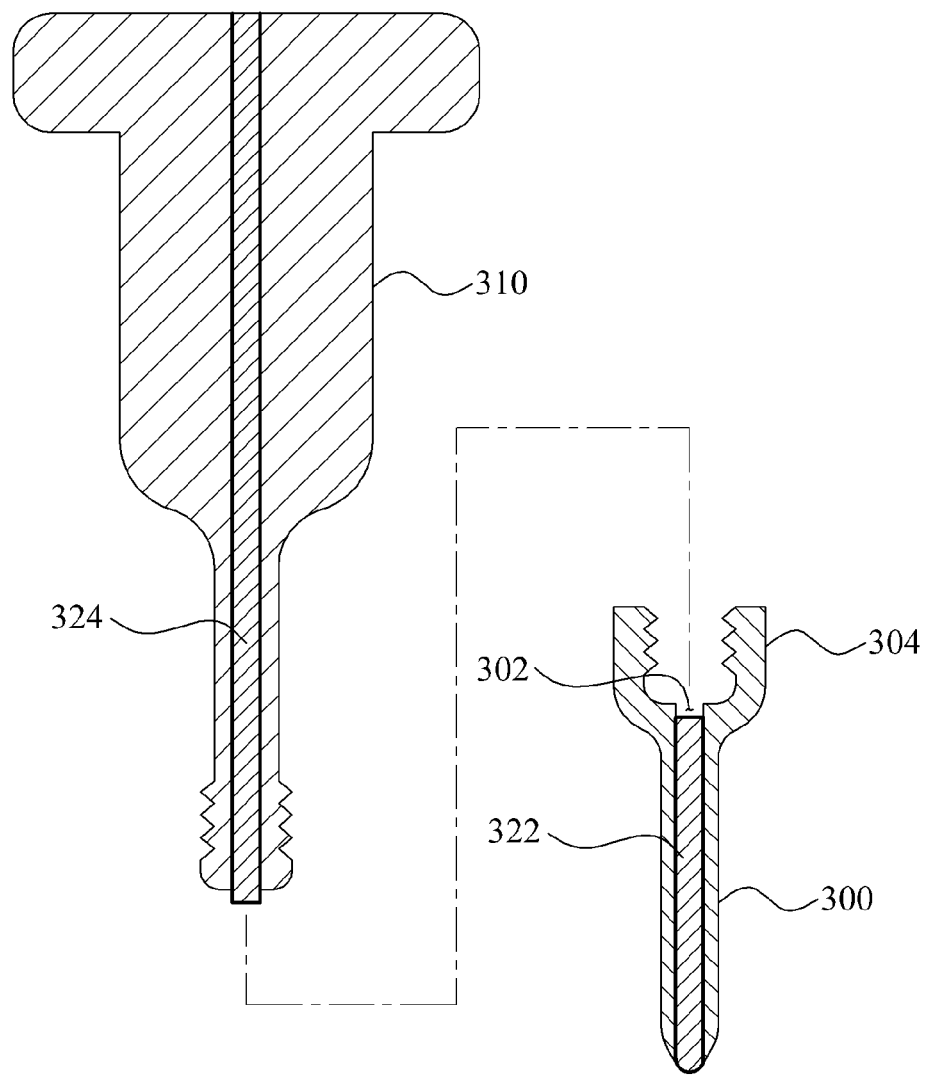
FIG. 10 is a view illustrating a medical insertion apparatus according to an embodiment of the present invention.
Figure 11:
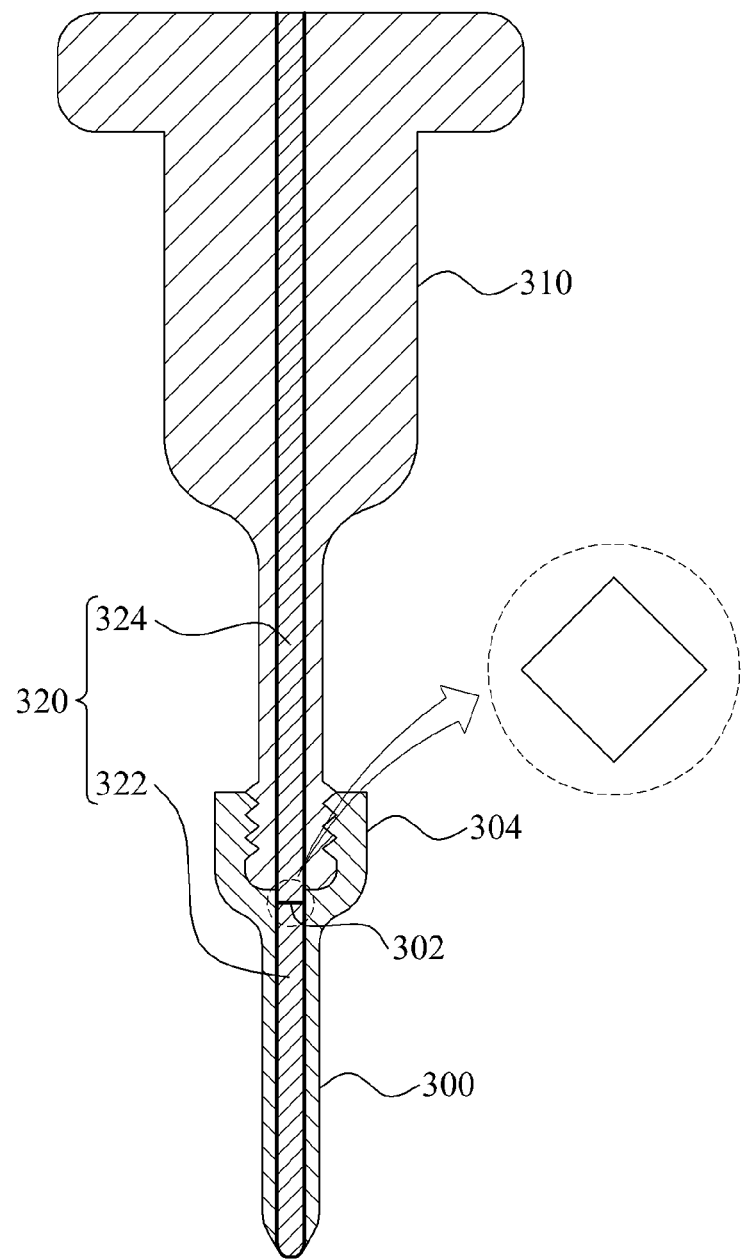
FIG. 11 is a view illustrating a connection between a screw body and a driver in a medical insertion apparatus according to an embodiment of the present invention.
Figure 12:
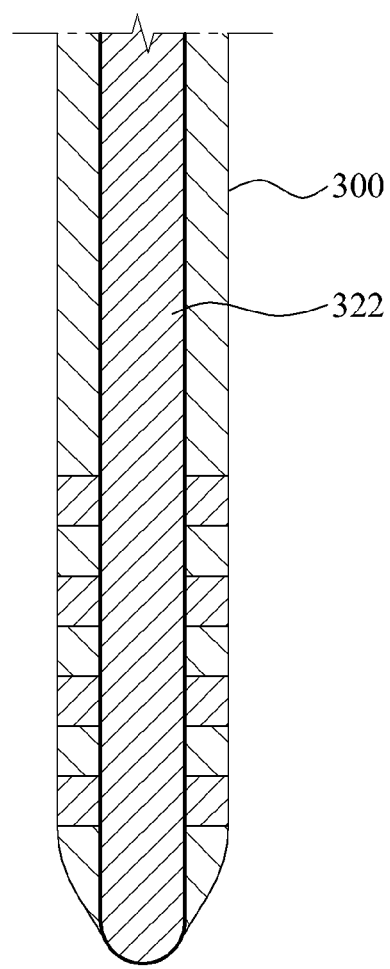
FIG. 12 is a view illustrating a conductive portion externally exposed at a portion of a screw body in a medical insertion apparatus according to an embodiment of the present invention.
Figure 13:
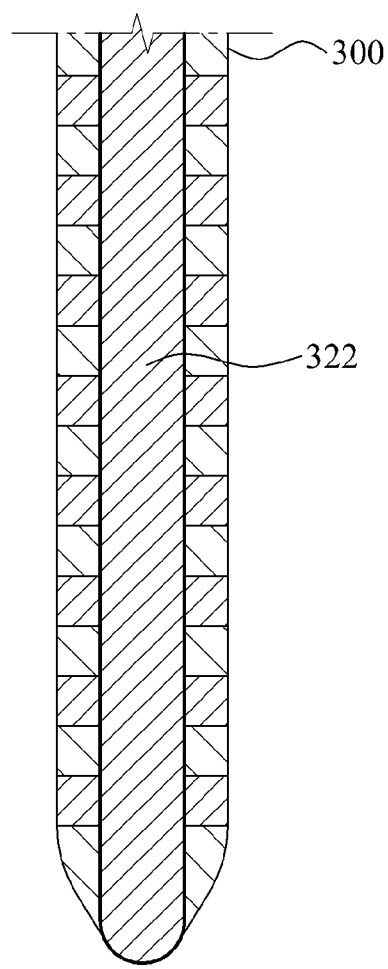
FIG. 13 is a view illustrating a conductive portion externally exposed over the entire screw body in a medical insertion apparatus according to an embodiment of the present invention.

FIG. 10 is a view illustrating a medical insertion apparatus 30 according to an embodiment of the present invention. FIG. 11 is a view illustrating a connection between a screw body 300 and a driver 310 in the medical insertion apparatus 30 according to an embodiment of the present invention. FIG. 12 is a view illustrating a conductive portion 320 externally exposed at a portion of the screw body 300 in the medical insertion apparatus 30 according to an embodiment of the present invention. FIG. 13 is a view illustrating the conductive portion 320 externally exposed over the entire screw body 300 in the medical insertion apparatus 30 according to an embodiment of the present invention.

Referring to FIG. 10, the medical insertion apparatus 30 includes a screw body 300, a driver 310, and a conductive portion 320.

The medical insertion apparatus 30 may be connected for use to a nerve stimulating and monitoring apparatus (not shown).

The nerve stimulating and monitoring apparatus may include an apparatus for EMG, an EP test, an MEP test, and an SSEP test.

However, the nerve stimulating and monitoring apparatus is not limited thereto. The nerve stimulating and monitoring apparatus may include any apparatus configured to provide an electrical stimulus to a muscle or nerve, and receive or detect a signal generated in the muscle or nerve in response to the electrical stimulus.

The nerve stimulating and monitoring apparatus may include a nerve stimulator and a stimulus receptor.

The nerve stimulator is a component that applies a minute current directly to a nerve, and the stimulus receptor is a component that detects a signal generated by a current in a nerve or muscle.

The conductive portion 320 provided in the medical insertion apparatus 30 may be connected directly to the nerve stimulator, thereby configuring a single electrode to apply a minute current directly to a nerve.

Accordingly, when the conductive portion 320 of the medical insertion apparatus 30 is inserted and in contact with a nerve during surgery or treatment, a current may be applied to the nerve and a signal may be generated in the nerve or muscle. When the generated signal is detected by the stimulus receptor, it may be verified that the medical insertion apparatus 30 is in contact with a nerve.

A configuration of the medical inserting apparatus 30 will be described in detail hereinafter.

The screw body 300 may be inserted into a body. A thread is provided on an outer circumferential surface of the screw body 300.

The screw body 300 may be inserted into a spine, a tooth, or a muscle. For example, the screw body 300 may be configured in a synostosis screw to be inserted into an osseous tissue adjacent to a nerve, in particular, a pedicle screw to be inserted into a spine.

Thus, the screw body 300 may be manufactured using titanium. Titanium is excellent in terms of biocompatibility and strength, and thus may be used as a material for a variety of implants.

A recess 302 is provided at a top end of the screw body 300.

An end portion of the driver 310 may be inserted into the recess 302 of the screw body 300.

Thus, the recess 302 is provided to have a shape corresponding to a shape of the end portion of the driver 310.

For example, a cross section of the recess 302 may be provided in a square form, a circular form, or a hexagonal form.

A protruding element 304 is provided at the top end of the screw body 300 to engage with the driver 310.

In detail, two protruding elements 304 may be provided at the top end of the screw body 300, and the driver 310 may be inserted between the two protruding elements 304. The protruding elements 304 may extend from the screw body 300 in lengths sufficient for engagement between the driver 310 and the screw body 300.

A thread may be provided on an inner side of the protruding element 304.

The thread of the protruding element 304 may be provided for screw fastening with the driver 310. A thread corresponding to the thread of the protruding element 304 may be provided on an outer side of the driver 310.

Through screw fastening between the thread provided on the protruding element 304 of the screw body 300 and the thread provided on the outer side of the driver 310, a tractive force may be produced between the screw body 300 and the driver 310 and thus, the driver 310 may be fastened to the screw body 300.

As described above, the driver 310 may be fastened to the top end of the screw body 300.

The driver 310 may engage with the screw body 300 to be used to fasten or loosen the screw body 300. The driver 310 may help the screw body 300 to be inserted into a body.

The end portion of the driver 310 may be provided in a shape corresponding to a shape of the recess 302 provided at the top end of the screw body 300, as described above.

The end portion of the driver 310 may be provided to protrude so as to be inserted into the recess 302 of the screw body 300.

A thread corresponding to the thread of the protruding element 304 of the screw body 300 may be provided on a side surface adjacent to the end portion of the driver 310.

The conductive portion 320 is provided in the screw body 300 and the driver 310 configured as described above.

The conductive portion 320 may detect a contact with a nerve when the screw body 300 is inserted into a body.

The conductive portion 320 includes a first conductor 322 and a second conductor 324.

The first conductor 322 is disposed in the screw body 300.

To dispose the first conductor 322, a hole (not shown) may be provided in a central portion of the screw body 300. The hole may be provided to penetrate through the screw body 300 from one end of the screw body 300 to a terminal portion of the screw body 300.

The first conductor 322 may be formed using a method of filling the hole with a melted material for the conductive portion 320 and hardening the material by cooling the material at room temperature.

For example, several protrusions or recesses may be formed on an inner circumferential surface of the hole, the hole may be filled with a melted material for the conductive portion 320, and the material may be hardened. In this example, the first conductor 322 may be more strongly fixed in the hole. Thus, the first conductor 322 may be stably disposed in the screw body 300.

A material of the first conductor 322 may include platinum, gold, silver, tungsten, and any material verified to be biocompatible and have an excellent electric conductivity and thus be suitable for detecting a minute signal.

The first conductor 322 is externally exposed in the recess 302 provided at the top end of the screw body 300, and connected to the second conductor 324.

The second conductor 324 is disposed in the driver 310.

The second conductor 324 extends in a longitudinal direction of the driver 310 from one end of the driver 310 to another end of the driver 310.

Similar to the first conductor 322, the second conductor 324 may be formed using a method of filling the hole with a melted material for the conductive portion 320 and hardening the material by cooling the material at room temperature.

The second conductor 324 is externally exposed at the end portion of the driver 310.

In detail, the second conductor 324 is externally exposed at a portion of the driver 310 to be inserted into the recess 302 provided at the top end of the screw body 300.

The second conductor 324 may also be externally exposed at a position to be connected to the nerve stimulating and monitoring apparatus in the driver.

Referring to FIG. 11, when the screw body 300 and the driver 310 are connected to each other, the first conductor 322 and the second conductor 324 may be electrically connected to each other as follows.

When the thread of the protruding element 304 of the screw body 300 and the thread of the driver 310 are connected to each other through screw fastening, a pushing force of the driver 310 may be produced toward the screw body 300. By the pushing force, the end portion of the driver 310 may be in contact with the recess 302 provided at the top end of the screw body 300.

In this example, the first conductor 322 provided in the screw body 300 is externally exposed in the recess 302. The second conductor 324 provided in the driver 310 is externally exposed at the end portion of the driver 310 to be inserted into the recess 302. Thus, the first conductor 322 and the second conductor 324 are in contact with each other.

Since a cross section of the recess 302 may be provided in a circular form, a square form, or a hexagonal form, the first conductor 322 and the second conductor 324 may be in surface contact with each other.

An electrical connection through the surface contact between the first conductor 322 and the second conductor 324 may prevent abrasion of the first conductor 322 and the second conductor 324, and increase a contact rate between the first conductor 322 and the second conductor 324.

In addition, the conductive portion 320 may be manufactured using various metals.

In detail, the first conductor 322 may be provided using a metal with relatively low sensitivity, for example, platinum, and tungsten. The second conductor 324 may be provided using a metal with excellent conductivity and strength, for example, platinum, and tungsten.

The conductive portion 320, in particular, the first conductor 322 may be externally exposed at various positions of the screw body 300.

As shown in FIG. 10 or 11, the first conductor 322 is externally exposed at the terminal portion of the screw body 300.

Since the first conductor 322 is externally exposed only at the terminal portion of the screw body 300, the medical insertion apparatus 30 may be manufactured through relatively simple molding.

In addition, the first conductor 322 is exposed at a portion of the screw body 300 to be in contact with a nerve first. Thus, a nerve may be detected relatively early when the medical insertion apparatus 30 is inserted into a body.

Referring to FIG. 12, the first conductor 322 is externally exposed at positions spaced apart from the terminal portion of the screw body 300.

The first conductor 322 is externally exposed over a half of the outer circumference of the screw body 300.

The first conductor 322 may extend to be perpendicular or to incline from the central portion of the screw body 300 toward the outer circumference of the screw body 300.

Referring to FIG. 13, the first conductor 322 is externally exposed over the entire outer circumference of the screw body 300.

Although not illustrated in detail, the externally exposed portions of the first conductor 322 may be provided in a form of ring shapes.

Through the conductive portion 320 configured as described above, the medical insertion apparatus 30 may monitor nerves in many ways by means of the screw body 300, thereby broadening a nerve monitoring range.

The medical insertion apparatus 30 may detect a contact with a nerve as follows.

The driver 310 and the screw body 300 may be connected to each other through screw fastening.

The thread of the driver 310 and the thread of the protruding element 304 of the screw body 300 may be fastened together through screw fastening.

In this example, the end portion of the driver 310 may be inserted into the recess 302 provided at the top end of the screw body 300.

Accordingly, the first conductor 322 and the second conductor 324 may be in surface contact with each other.

An electrical stimulus may be transmitted from the nerve stimulating and monitoring apparatus to the second conductor 324 of the driver 310.

When the electrical stimulus is transmitted to the second conductor 324, the electrical stimulus may be transmitted to the first conductor 322 electrically connected to the second conductor 324.

For example, when the screw body 300 is in contact with a nerve, an electrical stimulus may be transmitted to the nerve by the first conductor 322 externally exposed at the screw body 300.

The electrical stimulus transmitted to the nerve may be detected by the nerve stimulating and monitoring apparatus.

As described above, the medical insertion apparatus 30 may increase a contact rate of a conductive portion using a tractive force between a screw body and a driver, prevent abrasion of the conductive portion through a surface contact of the conductive portion, include the conductive portion to be manufactured using various metals, and effectively detect a nerve and prevent neurological damage by increasing an area of contact with nerves.

Figure 14:
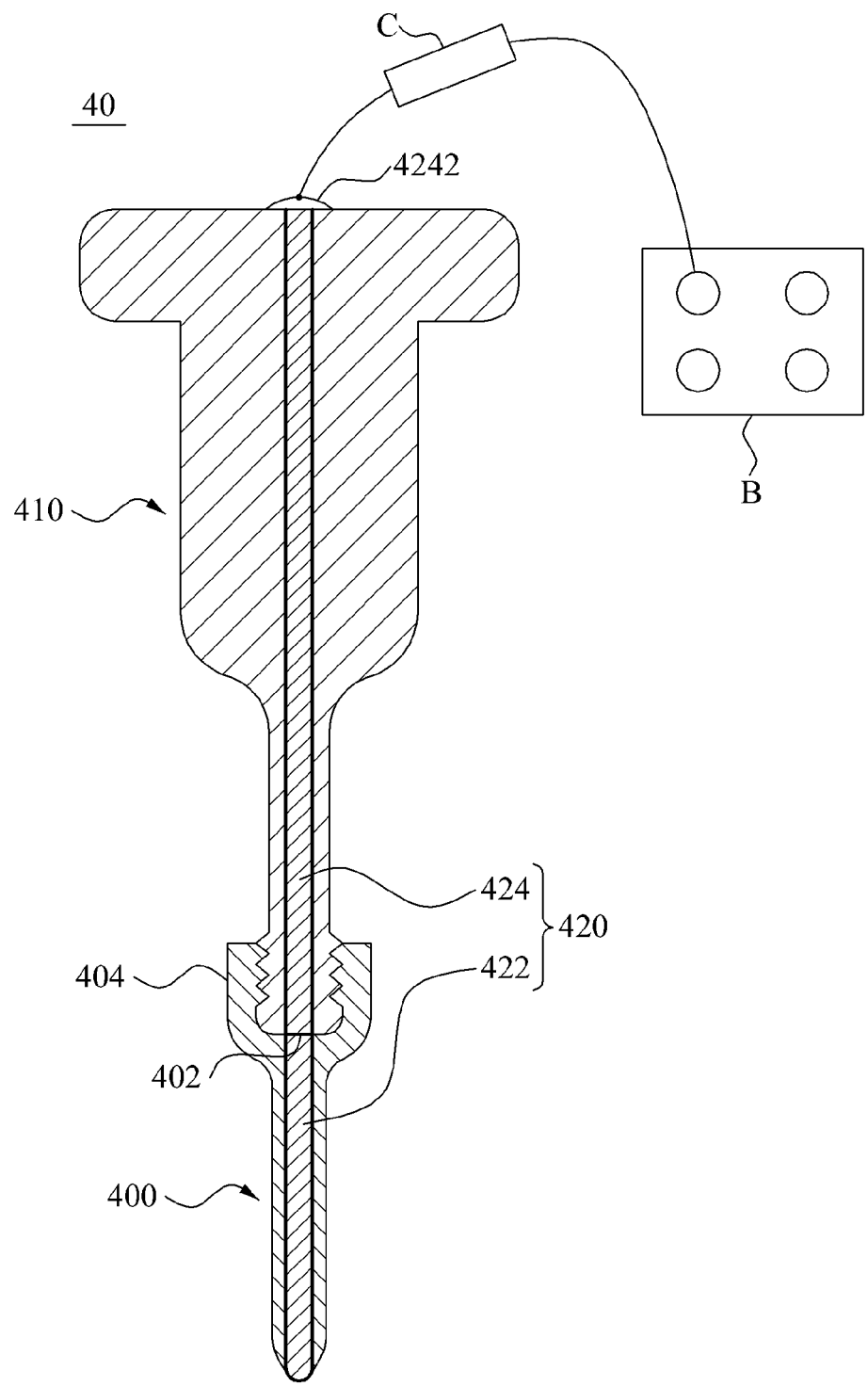
FIG. 14 is a view illustrating a medical insertion apparatus according to an embodiment of the present invention.
Figure 15:
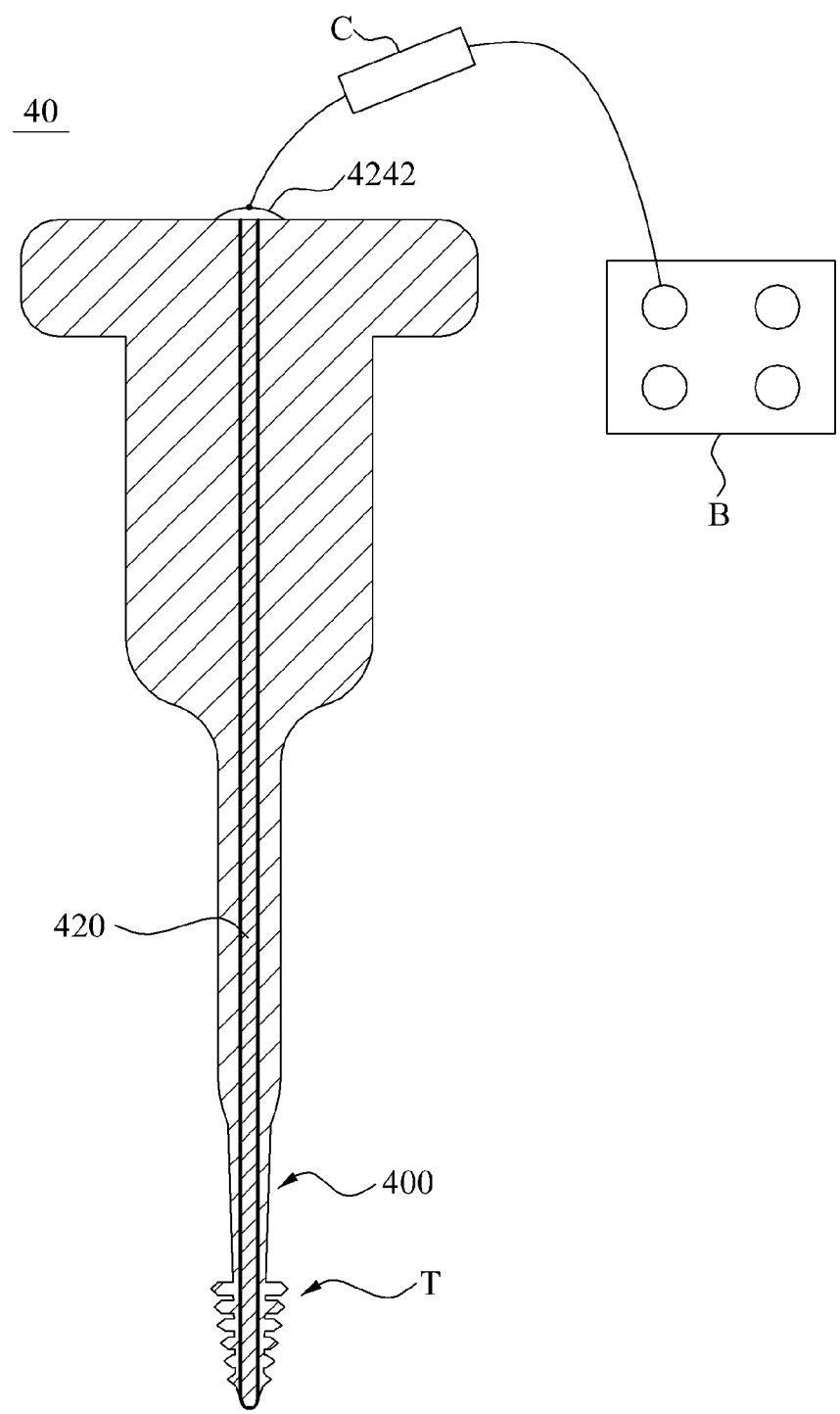
FIG. 15 is a view illustrating a screw body provided in a form of a tapping screw in a medical insertion apparatus according to an embodiment of the present invention.

FIG. 14 is a view illustrating a medical insertion apparatus 40 according to an embodiment of the present invention. FIG. 15 is a view illustrating a screw body 400 provided in a form of a tapping screw in the medical insertion apparatus 40 according to an embodiment of the present invention.

The medical insertion apparatus 40 may be connected for use to a nerve stimulating and monitoring apparatus B.

The nerve stimulating and monitoring apparatus B may include an apparatus for EMG, an EP test, an MEP test, and an SSEP test.

However, the nerve stimulating and monitoring apparatus B is not limited thereto. The nerve stimulating and monitoring apparatus B may include any apparatus configured to provide an electrical stimulus to a muscle or nerve, and receive or detect a signal generated in the muscle or nerve in response to the electrical stimulus.

The nerve stimulating and monitoring apparatus B may include a nerve stimulator and a stimulus receptor.

The nerve stimulator is a component that applies a minute current directly to a nerve, and the stimulus receptor is a component that detects a signal generated by a current in a nerve or muscle.

Accordingly, when a conductive portion 420 of the medical insertion apparatus 40 is inserted and in contact with a nerve during surgery or treatment, a current may be applied to the nerve and a signal may be generated in the nerve or muscle. When the generated signal is detected by the stimulus receptor, it may be verified that the medical insertion apparatus 40 is in contact with a nerve.

The medical insertion apparatus 40 may be connected in a wired or wireless manner to the nerve stimulating and monitoring apparatus B. A configuration of the medical insertion apparatus 40 will be described in detail hereinafter.

Referring to FIG. 14, the medical insertion apparatus 40 includes the screw body 400, a driver 410, and the conductive portion 420.

The screw body 400 may be inserted into a body. A thread may be provided on an outer side of the screw body 400.

The screw body 400 may be inserted into a spine, a tooth, or a muscle. For example, the screw body 400 may be configured in a synostosis screw to be inserted into an osseous tissue adjacent to a nerve, in particular, a pedicle screw to be inserted into a spine.

Thus, the screw body 400 may be manufactured using titanium. Titanium is excellent in terms of biocompatibility and strength, and thus used as a material for a variety of implants.

A recess 402 is provided at a top end of the screw body 400.

An end portion of the driver 410 may be inserted into the recess 402 of the screw body 400.

Thus, the recess 402 is provided to have a shape corresponding to a shape of the end portion of the driver 410.

For example, a cross section of the recess 402 may be provided in a square form, a circular form, or a hexagonal form.

A protruding element 404 is provided at the top end of the screw body 400 to engage with the driver 410.

In detail, two protruding elements 404 may be provided at the top end of the screw body 400, and the driver 410 may be inserted between the two protruding elements 404. The protruding elements 404 may extend from the screw body 400 in lengths sufficient for engagement between the driver 410 and the screw body 400.

A thread may be provided on an inner side of the protruding element 404.

The thread of the protruding element 404 may be provided for screw fastening with the driver 410. A thread corresponding to the thread of the protruding element 404 may be provided on an outer side of the driver 410.

Through screw fastening between the thread provided on the protruding element 404 of the screw body 400 and the thread provided on the outer side of the driver 410, a tractive force may be produced between the screw body 400 and the driver 410 and thus, the driver 410 may be fastened to the screw body 400.

As described above, the driver 410 may be fastened to the top end of the screw body 400.

The driver 410 may engage with the screw body 400 to be used to fasten or loosen the screw body 400. The driver 410 may help the screw body 400 to be inserted into a body.

The end portion of the driver 410 may be provided in a shape corresponding to a shape of the recess 402 provided at the top end of the screw body 400, as described above.

The end portion of the driver 410 may be provided to protrude so as to be inserted into the recess 402 of the screw body 400.

A thread corresponding to the thread of the protruding element 404 of the screw body 400 may be provided on a side surface adjacent to the end portion of the driver 410.

Referring to FIG. 15, the screw body 400 is provided in a form of a tapping screw T.

The tapping screw T may be used to perform boring before the screw body 400 is inserted into a body.

The screw body 400 may be inserted into a body more safely through a hole provided by the tapping screw T.

When the screw body 400 is provided in a form of a tapping screw T, the screw body 400 and the driver 410 may be integrally provided.

The conductive portion 420 is provided to be externally exposed on a side surface on which the tapping screw T is provided. Thus, a contact between the screw body 400 and a nerve may be detected during the boring process.

The conductive portion 420 is provided in the screw body 400 and the driver 410 configured as described above.

The conductive portion 430 may detect a contact with a nerve when the screw body 400 is inserted into a body.

The conductive portion 420 includes a first conductor 422 and a second conductor 424.

The first conductor 422 is disposed in the screw body 400.

To dispose the first conductor 422, a hole (not shown) may be provided in a central portion of the screw body 400. The hole may be provided to penetrate through the screw body 400 from one end of the screw body 400 to a terminal portion of the screw body 400.

The first conductor 422 may be formed using a method of filling the hole with a melted material for the conductive portion 420 and hardening the material by cooling the material at room temperature.

For example, several protrusions or recesses may be formed on an inner circumferential surface of the hole, the hole may be filled with a melted material for the conductive portion 420, and the material may be hardened. In this example, the first conductor 422 may be more strongly fixed in the hole. Thus, the first conductor 422 may be stably disposed in the screw body 400.

A material of the first conductor 422 may include platinum, gold, silver, tungsten, and any material verified to be biocompatible and have an excellent electric conductivity and thus be suitable for detecting a minute signal.

The first conductor 422 is externally exposed in the recess 402 provided at the top end of the screw body 400, and connected to the second conductor 424.

The second conductor 424 is disposed in the driver 410.

The second conductor 424 extends in a longitudinal direction of the driver 410 from one end of the driver 410 to another end of the driver 410.

Similar to the first conductor 422, the second conductor 424 may be formed using a method of filling the hole with a melted material for the conductive portion 420 and hardening the material by cooling the material at room temperature.

The second conductor 424 is externally exposed at the end portion of the driver 410.

In detail, the second conductor 424 is externally exposed at a portion of the driver 410 to be inserted into the recess 402 provided at the top end of the screw body 400. The second conductor 424 is externally exposed to be electrically connected to the first conductor 422.

In addition, the second conductor 424 includes an exposed terminal 4242 at an end portion of the driver 410.

The exposed terminal 4242 is an externally exposed portion of the second conductor 424, and is to be connected via wire to the nerve stimulating and monitoring apparatus B.

Thus, the exposed terminal 4242 is externally exposed at a position to be connected to the nerve stimulating and monitoring apparatus B in the driver 410.

FIG. 14 illustrates the exposed terminal 4242 being provided at the end portion of the driver 410. However, a position at which the exposed terminal 4242 is provided is not limited thereto. The exposed terminal 4242 may be provided on a side surface of the driver 410.

When the screw body 400 and the driver 410 are connected to each other, the first conductor 422 and the second conductor 424 may be electrically connected to each other.

When the thread of the protruding element 404 of the screw body 400 and the thread of the driver 410 are connected to each other through screw fastening, a pushing force of the driver 410 may be produced toward the screw body 400. By the pushing force, the end portion of the driver 410 may be in contact with the recess 402 provided at the top end of the screw body 400.

In this example, the first conductor 422 provided in the screw body 400 is externally exposed in the recess 402. The second conductor 424 provided in the driver 410 is externally exposed at the end portion of the driver 410 to be inserted into the recess 402. Thus, the first conductor 422 and the second conductor 424 are in contact with each other.

Since a cross section of the recess 402 may be provided in a circular form, a square form, or a hexagonal form, the first conductor 422 and the second conductor 424 may be in surface contact with each other.

An electrical connection through the surface contact between the first conductor 422 and the second conductor 424 may prevent abrasion of the first conductor 422 and the second conductor 424, and increase a contact rate between the first conductor 422 and the second conductor 424.

The conductive portion 420, in particular, the first conductor 422 may be externally exposed at various positions of the screw body 400.

The first conductor 422 is externally exposed at the terminal portion of the screw body 400.

In detail, the first conductor 422 extends in a longitudinal direction of the screw body 400 from one end of the screw body 400 to the terminal portion of the screw body 400.

Since the first conductor 422 is externally exposed only at the terminal portion of the screw body 400, the medical insertion apparatus 40 may be manufactured through relatively simple molding.

In addition, the first conductor 422 is exposed at a portion of the screw body 400 to be in contact with a nerve first. Thus, a nerve may be detected relatively early when the medical insertion apparatus 40 is inserted into a body.

The first conductor 422 may be externally exposed at a position spaced apart from the terminal portion of the screw body 400.

The first conductor 422 may be externally exposed over one-half of the outer circumference of the screw body 400.

The first conductor 422 may extend to be perpendicular or to incline from the central portion of the screw body 400 toward the outer circumference of the screw body 400.

The first conductor 422 may also be externally exposed over the entire outer circumference of the screw body 400.

Although not illustrated in detail, the externally exposed portions of the first conductor 422 may be provided in a form of ring shapes.

Through the conductive portion 420 configured as described above, the medical insertion apparatus 40 may monitor nerves in many ways by means of the screw body 400, thereby broadening a nerve monitoring range.

The medical insertion apparatus 40 may detect a contact with a nerve as follows.

The driver 410 and the screw body 400 may be connected to each other through screw fastening.

The thread of the driver 410 and the thread of the protruding element 404 of the screw body 400 may be fastened together through screw fastening.

In this example, the end portion of the driver 410 may be inserted into the recess 402 provided at the top end of the screw body 400.

Accordingly, the first conductor 422 and the second conductor 424 may be in surface contact with each other.

An electrical stimulus may be transmitted from the nerve stimulating and monitoring apparatus B to the second conductor 424 of the driver 410.

In detail, a trigger apparatus C is connected to the nerve stimulating and monitoring apparatus B.

The trigger apparatus C refers to an apparatus that automatically initiates an operation of an electronic circuit, a machine, or a program to be used to achieve a predetermined stable state. The trigger apparatus C may transmit an electric stimulus generated by the nerve stimulating and monitoring apparatus B to the second conductor 424.

By providing the exposed terminal 4242 on the driver 410 and contacting an end portion of the trigger apparatus C to the exposed terminal 4242, the electrical stimulus may be easily transmitted from the nerve stimulating and monitoring apparatus B to the conductive portion 420.

When the electrical stimulus is transmitted to the second conductor 424, the electrical stimulus may be transmitted to the first conductor 422 electrically connected to the second conductor 424.

For example, when the screw body 400 is in contact with a nerve, an electrical stimulus may be transmitted to the nerve by the first conductor 422 externally exposed at the screw body 400.

The electrical stimulus transmitted to the nerve may be detected by the nerve stimulating and monitoring apparatus B.

As described above, the medical insertion apparatus 40 may increase a surgical stability, reduce a radiation exposure time during surgery, and be compatible with an existing nerve stimulating and monitoring apparatus without using separate equipment. In addition, the medical insertion apparatus 40 may include an exposed terminal to easily connect a conductive portion to a nerve stimulating and monitoring apparatus.

Hereinafter, a medical insertion apparatus 50 to be connected wirelessly to the nerve stimulating and monitoring apparatus B according to an embodiment will be described. Descriptions on a configuration substantially identical or similar to the configuration of the medical insertion apparatus 40 will be omitted for conciseness.

Figure 16:
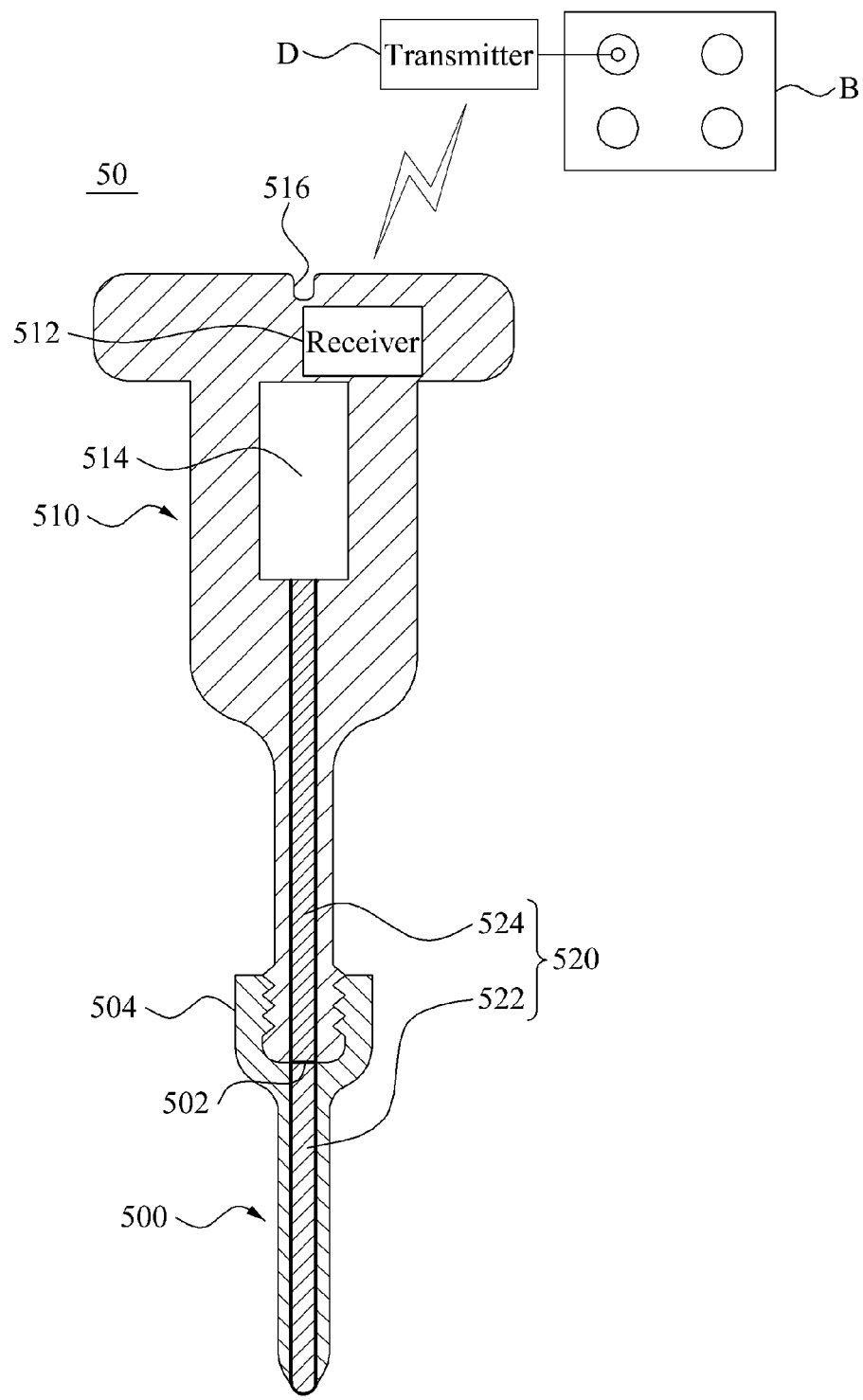
FIG. 16 is a view illustrating a medical insertion apparatus according to an embodiment of the present invention.
Figure 17:
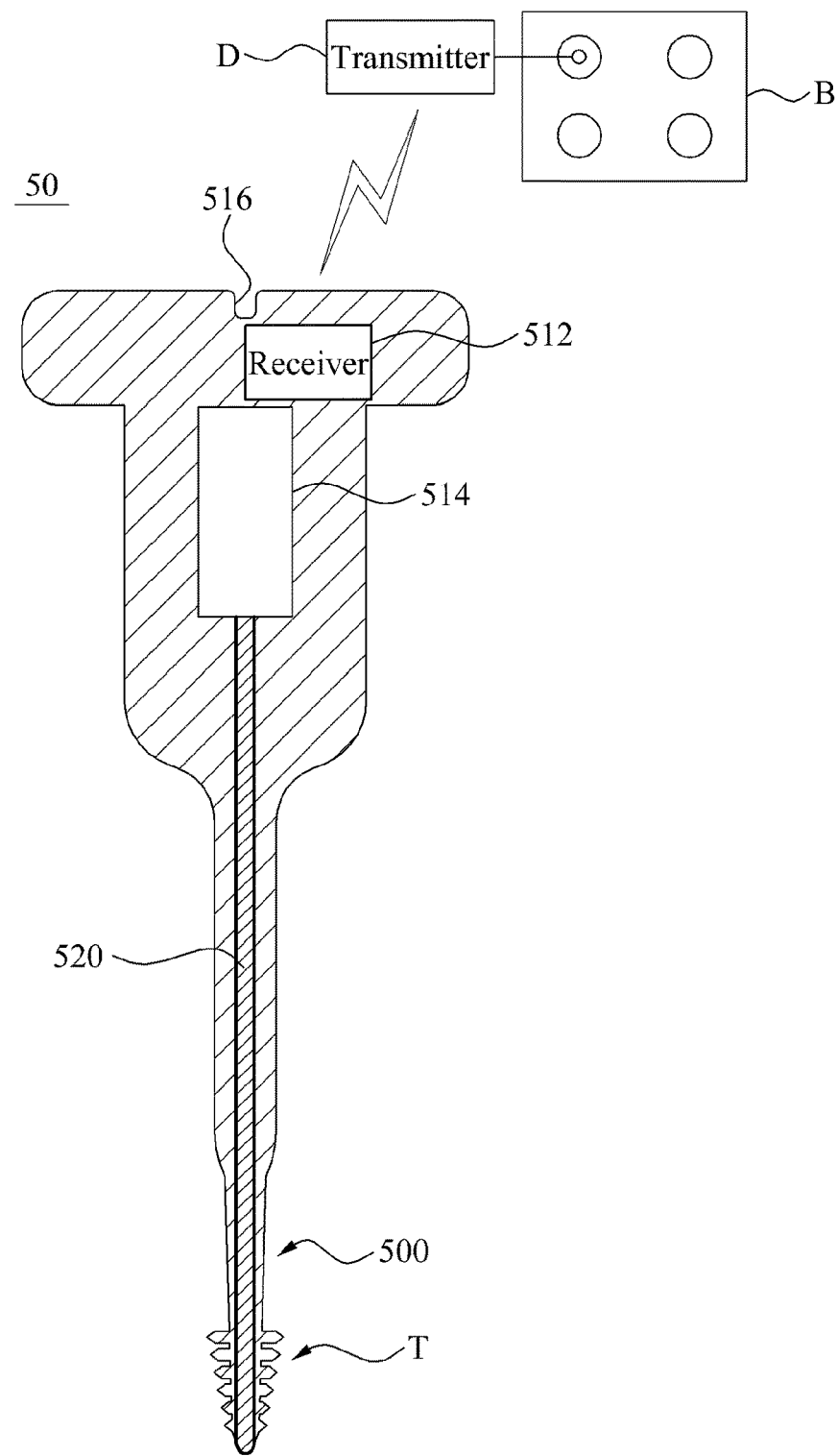
FIG. 17 is a view illustrating a screw body provided in a form of a tapping screw in a medical insertion apparatus according to an embodiment of the present invention.
Figure 18:
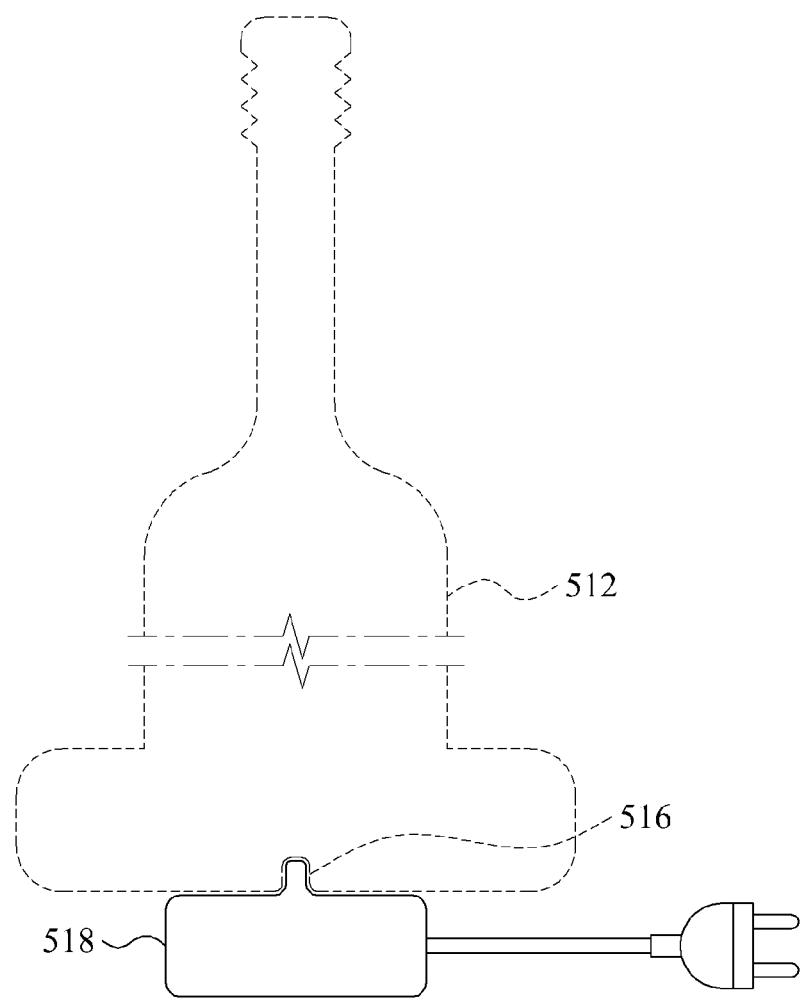
FIG. 18 is a view illustrating a driver being charged in a medical insertion apparatus according to an embodiment of the present invention.

FIG. 16 is a view illustrating the medical insertion apparatus 50 according to an embodiment of the present invention. FIG. 17 is a view illustrating a screw body 500 provided in a form of a tapping screw in the medical insertion apparatus 50 according to an embodiment of the present invention. FIG. 18 is a view illustrating a driver 510 being charged in the medical insertion apparatus 50 according to an embodiment of the present invention.

Referring to FIG. 16, the medical insertion apparatus 50 includes the screw body 500, the driver 510, and a conductive portion 520.

The medical insertion apparatus 50 differs from the medical insertion apparatus 40 in that the medical insertion apparatus 50 is connected wirelessly to a nerve stimulating and monitoring apparatus.

The driver 510 includes a receiver 512, and the nerve stimulating and monitoring apparatus B includes a transmitter D.

An electrical stimulus generated by the nerve stimulating and monitoring apparatus B may be transmitted wirelessly from the transmitter D to the receiver 512 of the driver 510.

The driver 510 further includes an embedded battery 514.

The second conductor 524 is connected to the embedded battery 514.

In the driver 510, the second conductor 524 extends in a longitudinal direction of the driver 510 from the embedded battery 514 to the end portion of the driver 510 engaging with the screw body 500.

To charge the embedded battery 514, a charging socket 516 is provided at the end portion of the driver 510.

Referring to FIG. 17, when the screw body 500 is provided in a form of a tapping screw T, the screw body 500 and the driver 510 are integrally provided.

The receiver 512 is provided to wirelessly detect a contact between the screw body 500 and a nerve when performing boring before the screw body 500 is inserted into a body.

The embedded battery 514 may also be provided in the screw body 500, and the charging socket 516 may also be provided at the end portion of the screw body 500. In this example, the screw body 500 may be charged for use as necessary.

Referring to FIG. 18, the charging socket 516 is disposed on a charging stand 518.

The charging stand 518 is provided in a shape corresponding to a shape of the charging socket 516.

When the charging socket 516 is disposed on the charging stand 518 and an electric plug connected to the charging stand 518 is inserted into an outlet, the embedded battery 514 provided in the driver 510 may be charged.

As described above, the medical insertion apparatus 50 may wirelessly monitor a nerve through a receiver included in a driver, reduce an inconvenience that a surgeon may experience due to a wire, and easily charge an embedded battery included in the driver by disposing the driver on a charging stand.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A medical insertion apparatus comprising:
    a screw body to be inserted into a body;
    a driver to engage with the screw body to be used to fasten or loosen the screw body; and
    a conductive portion provided by the screw body and the driver,
    wherein the conductive portion provided by the screw body and the conductive portion provided by the driver are electrically connected to each other, and
    wherein the conductive portion of the screw body is a wire externally exposed and extending straightly along an outer circumferential surface of the screw body from a top end of the screw body to a central portion of a terminal portion of the screw body, the wire being parallel to the longitudinal axis of the screw body,
    a visual element on the driver for visually indicating a position of the wire along the outer circumferential surface of the screw body, the visual element disposed in a position aligned with the position of the wire, and
    wherein by verifying the position of the visual element, the position of the wire when the screw body is inserted into the body is verified.

2. The medical insertion apparatus of claim 1, wherein a recess into which an end portion of the driver is to be inserted is provided in the screw body.

3. The medical insertion apparatus of claim 1, further comprising:
    a nerve stimulating and monitoring apparatus to transmit an electrical stimulus to the conductive portion or detect a signal generated by the electrical stimulus.

4. The medical insertion apparatus of claim 3, wherein the conductive portion comprises an exposed terminal at one end of the driver, and
    the nerve stimulating and monitoring apparatus is connected to the exposed terminal.

5. The medical insertion apparatus of claim 3, wherein a transmitter is provided in the nerve stimulating and monitoring apparatus, and a receiver is provided in the driver.

6. The medical insertion apparatus of claim 1, wherein an embedded battery is provided in the driver, a charging socket is provided at one end of the driver to charge the embedded battery, and the medical insertion apparatus further comprises a charging stand on which the charging socket is to be disposed.

* * * * *